United States Patent [19]
Bell

[11] Patent Number: 5,473,778
[45] Date of Patent: Dec. 12, 1995

[54] SUNGLASS CAP

[75] Inventor: Roland M. Bell, Ottawa, Kans.

[73] Assignee: John E. Pollock, Edgerton, Kans.

[21] Appl. No.: 175,144

[22] Filed: Dec. 29, 1993

[51] Int. Cl.⁶ ........................................ A61F 9/00
[52] U.S. Cl. .................. 2/10; 2/195.1; 2/209.13; 351/155
[58] Field of Search .................. 2/10, 171, 172, 2/181, 181.2, 181.4, 181.6, 181.8, 175.1, 195.1, 209.13, 209.14; 351/155

[56] References Cited

U.S. PATENT DOCUMENTS

| | | | |
|---|---|---|---|
| 2,274,222 | 2/1942 | Tedrow | 2/10 |
| 3,833,300 | 9/1974 | Rymes | 2/10 |

OTHER PUBLICATIONS

Preliminary Patent Search Results (see attached).

Primary Examiner—Diana Biefeld
Attorney, Agent, or Firm—Chase & Yakimo

[57] ABSTRACT

A sunglass system comprises a pocket releasably attached to the interior of a crown of a cap so as to present an access opening adjacent the cap visor. Upon cap positioning on the head of a user, a lens, positioned within the pocket, is user slidable between a first position above the eyes of the user and a second position below the cap visor and adjacent the eyes of the wearer. The lens is maintained at its second position by laterally extending tabs engaging the lower portion of the pocket and at its first position within the pocket by a releasable friction fit among the pocket, lens and cap crown.

12 Claims, 4 Drawing Sheets

FIG.2
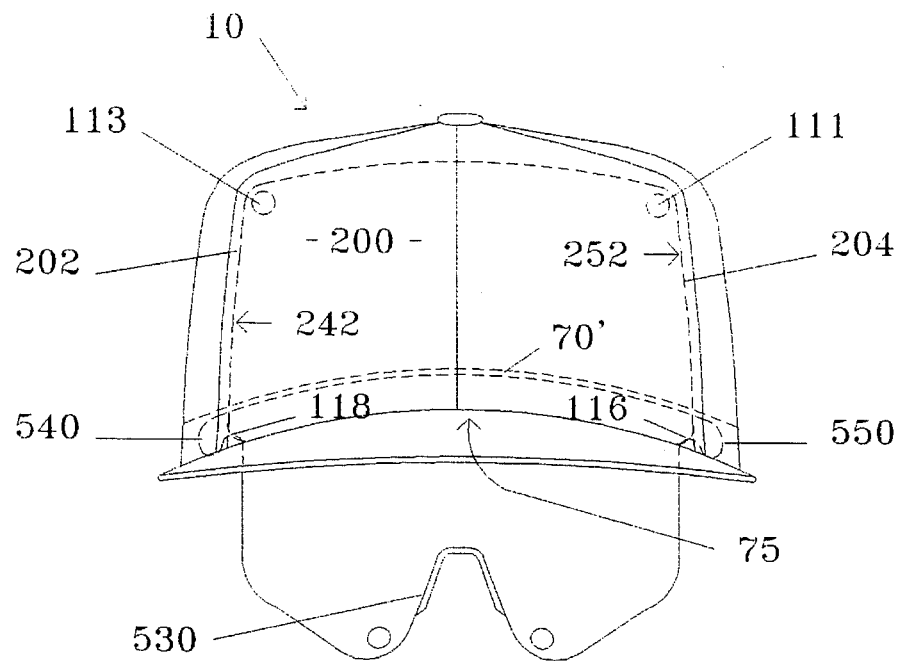
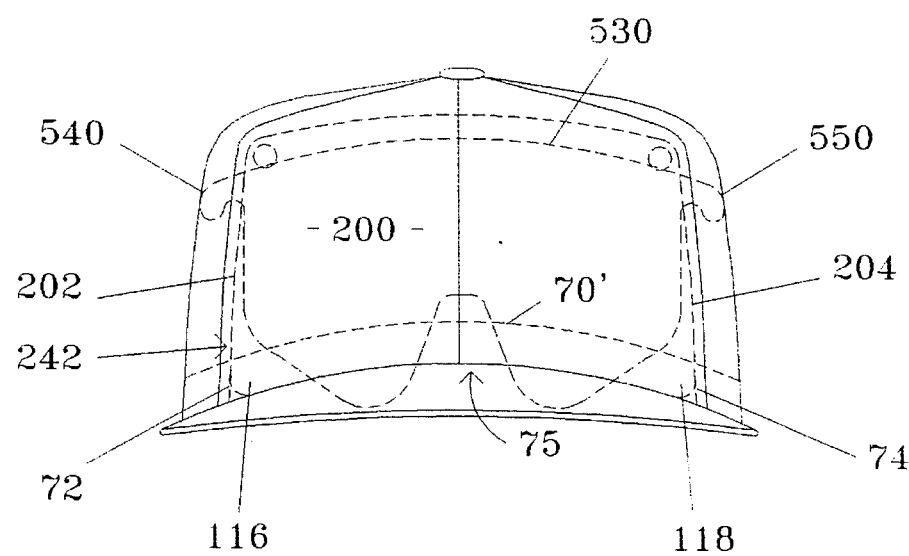
FIG.3

FIG. 4
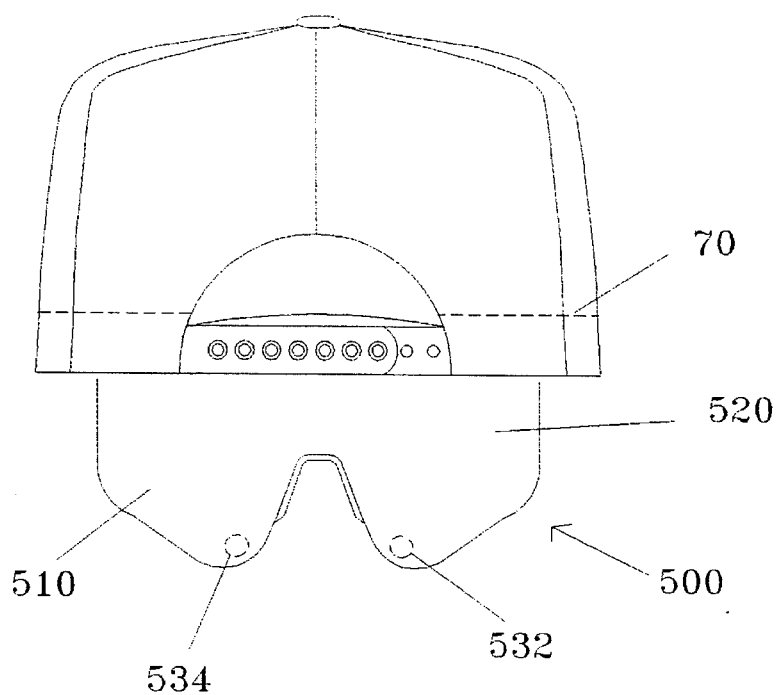
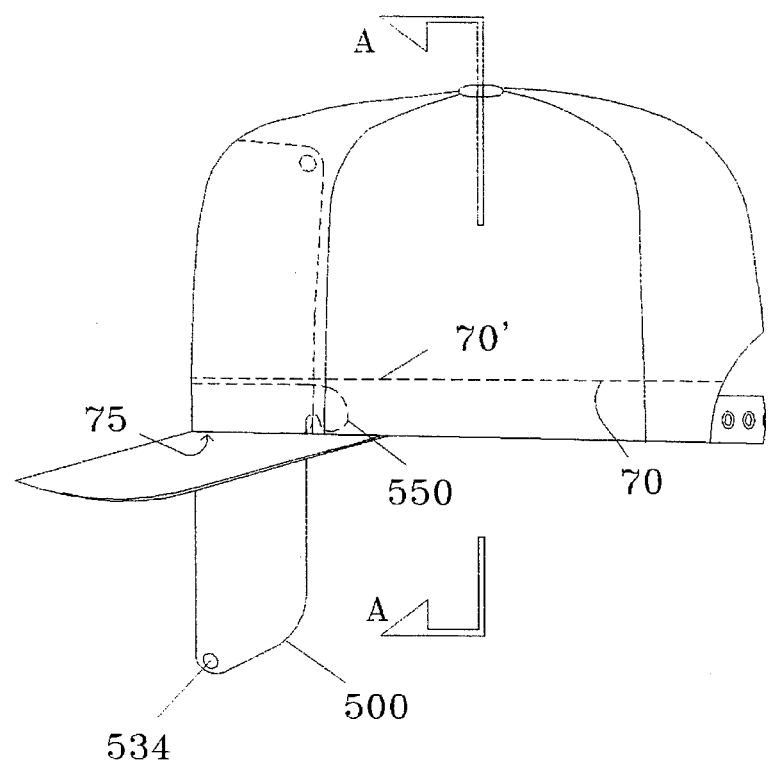
FIG. 5

FIG. 6
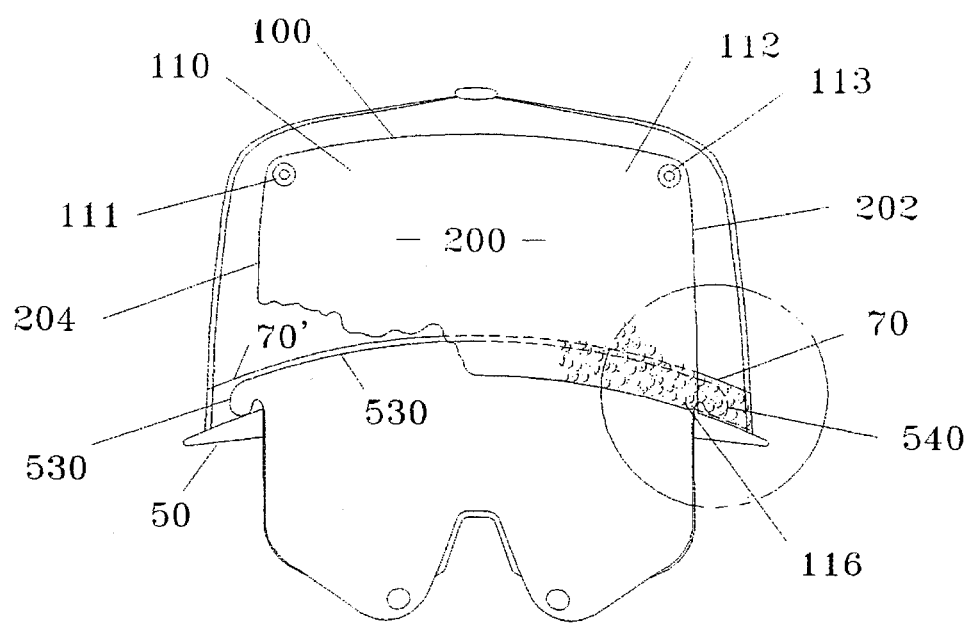
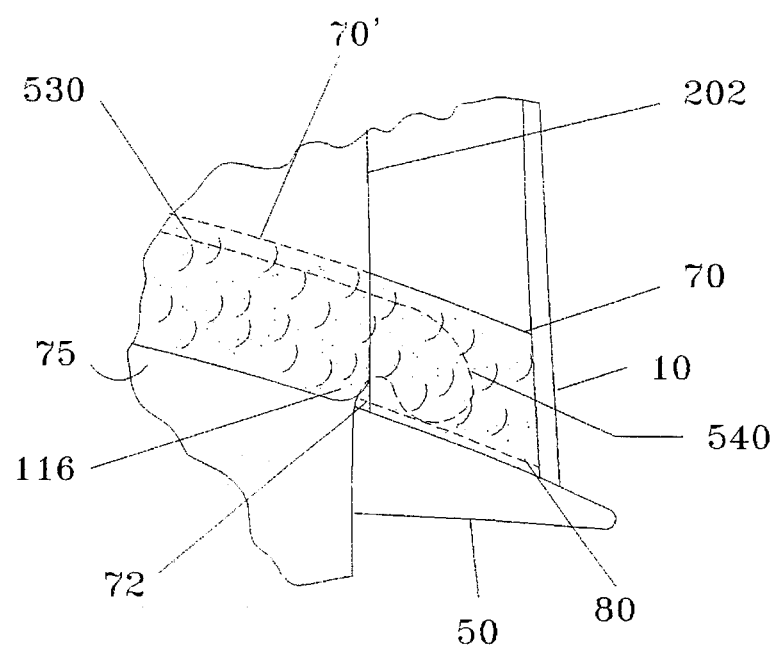
FIG. 7

SUNGLASS CAP

BACKGROUND OF THE INVENTION

This invention relates to a cap with sunglasses and more particularly to a lens that is user slidable between a first storage position in a pocket in the cap crown and a second functional position adjacent the eyes of the wearer.

It is desirable, particularly when outdoors, to use a cap and sunglasses as a shield against the sun's rays. The sunglasses are preferably movable between nonfunctional and functional positions depending on the sun's presence and/or location. Various structures are known which clip sunglasses to a visor of a cap such that the sunglasses are user pivotable between a first nonfunctional position adjacent the bill of the cap and a second position normal thereto in front of the eyes of the wearer. Although assumably effective in operation, such devices can be cumbersome to use, relatively complex in construction, high in cost and when not in use are preferably separated from the cap itself.

In response thereto I provide a cap having a lens pocket attached to the crown area. Entrance to the pocket is presented by a slot adjacent the bill of the cap. A lens is inserted in the pocket and is user slidable between a first position at which the lens is maintained within the pocket and a second position at which the lens extends from the pocket at a position adjacent the eyes of the wearer. Upon user exertion of a downward force on the pocketed lens, the lens slides through the pocket and out the slot until tabs at the opposed lateral sides of the lens engage the lateral edges of the pocket. This engagement positions the lens in front of the eyes of the wearer. During nonuse the lens is user-slidable in an opposed direction into the pocket and held therein by the interface between the pocket and the lens.

It is therefor a general object of this invention to provide a cap having a lens movable between a first storage position and a second functional position.

Another object of the invention is to provide a device, as aforesaid, presenting a pocket therein for releasably holding the lens in a storage position.

A further object of this invention is to provide a device, as aforesaid, which maintains the lens in either a first nonfunctional position or a second functional position.

Still another object of this invention is to provide a device, as aforesaid, in which the lens is user slidable between said first and second positions when positioned on the head of a wearer.

A further particular object of this invention is to provide a device, as aforesaid, which allows for interchangeability of various lenses.

Other objects and advantages of this invention will become apparent from the following description taken in connection with the accompanying drawings, wherein is set forth by way of illustration and example, an embodiment of this invention.

BRIEF DESCRIPTION OF THE DRAWINGS

FIG. 2 is a front view of the cap with lens in a functional position;

FIG. 3 is a front view of the cap with lens in a storage position;

FIG. 4 is a rear view of the cap with lens in the functional position;

FIG. 5 is a side view of the cap with lens in the functional position;

FIG. 6 is a rear fragmentary view of the cap, taken along line A—A in FIG. 5, with a portion of the pocket broken away to show the lens in an extended position;

FIG. 7 is an enlarged fragmentary view of the encircled portion of the cap in FIG. 6 showing the relationship among the pocket, lens and cap band.

DESCRIPTION OF THE PREFERRED EMBODIMENT

Figure 1:
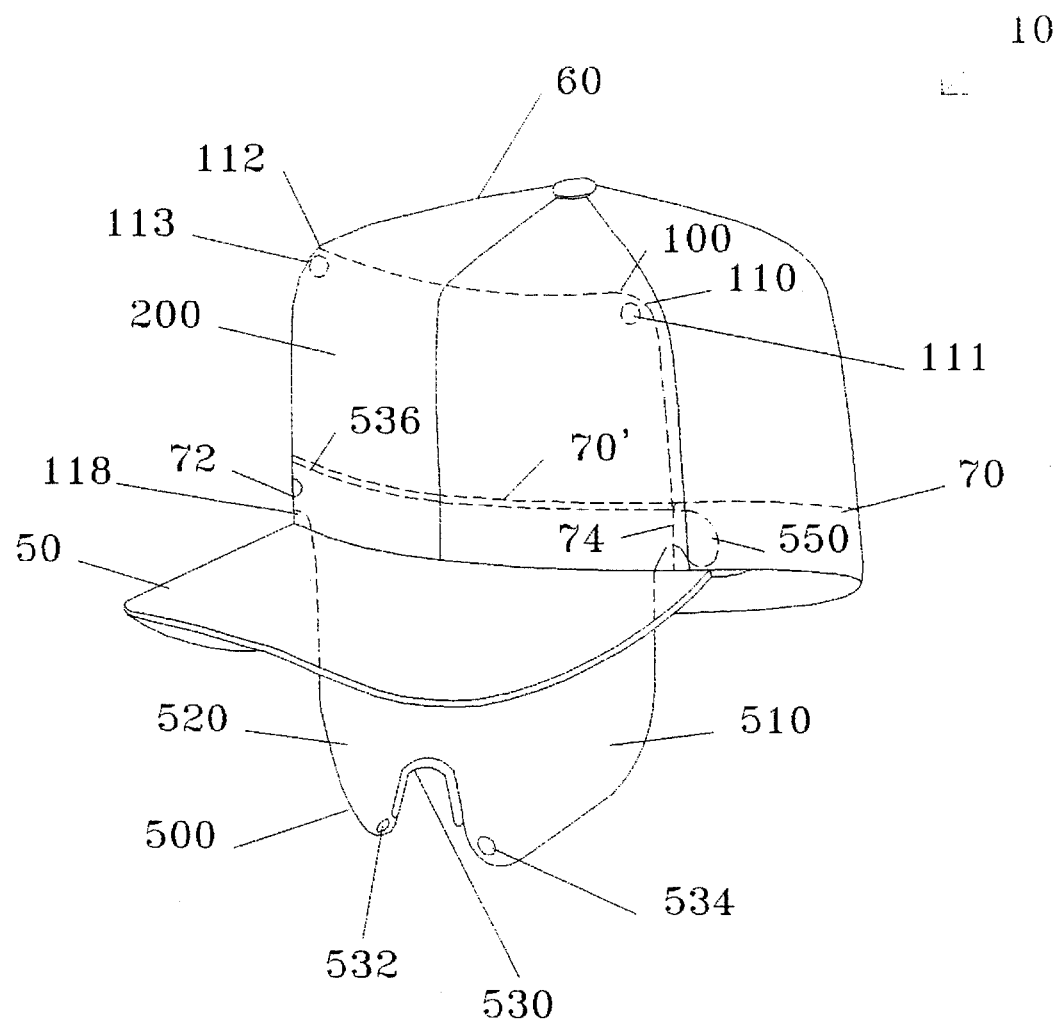
FIG. 1 is a perspective view showing the cap with lens in a functional position.

Turning more particularly to the drawings, a representative headpiece is shown as a cap 10 with a bill/visor 50 forwardly extending from the crown 60. Secured about the circumference of the lower edge of cap 10 by stitching 80 (FIG. 7) is a band 70. The band 70 stitching 80 about the cap circumference is interrupted at first 72 and second 74 laterally displaced positions adjacent the bill 50 such that the band 70' material therebetween and cap 10 material form a slot 75. It is understood that band portion 70' may be omitted if so desired.

A generally rectangular flap 100 made of terry cloth or the like is attached to the interior of the cap crown 60 at the upper corners 110 and 112. Corners 110, 112 may be secured to cap 10 by either permanent stitching, snap combinations 111, 113 or by Velcro® fastener combinations. The lower corners 116, 118 of the flap 100 preferably have appropriate fasteners thereon, e.g. Velcro®, allowing for a releasable fastening of these corners 116, 118 of flap 100 to the underlying band 70' or directly to the hat if band 70' portion is not used. Accordingly, upon such corner fastening the flap 100 cooperates with the inner material of crown 60 to form a pocket 200 with access therein provided by slot 75. The lateral edges 202, 204 of the pocket 200 are displaced from the underlying crown 60 material for a purpose to be subsequently described.

The lens 500, as shown in FIG. 3, has a radius which approaches the radius of the band 70' adjacent the bill 50. Lens 500 presents first 510 and second 520 eye portions with a padded 532, 534 notch 530 therebetween for resting on the bridge of the wearer's nose. Extending from the lateral ends of the upper edge 536 of lens 500 are laterally extending tabs 540, 550.

Prior to use the lens 500 is placed through the slot 75 of pocket 200 and subsequently maneuvered such that the tabs 540, 550 laterally extend beyond the lateral edges 202, 204 of the pocket 200 (FIG. 3). Accordingly, the tabs 540, 550 are free to slide beneath the lateral edges 202, 204 as displaced from the underlying crown 60 material. The lower corners 116, 118 of the flap 100 are then secured to the band 70' by the engagement of the respective mating fasteners. Slidable movement of the lens 500 in an upward direction is restrained by contact of the flap 100 fasteners 111, 113 with the upper lens edge 530. At this position the close relationship among the flap 100 and underlying crown 60 material holds the intermediate lens 500 in pocket 200 by a friction fit relationship therebetween.

In use the cap 10 is placed upon the head of the user with the lens 500 being held within the pocket 200 by the above-described friction fit among the flap 100, lens 500 and cap crown 60. Upon user exertion of a sufficient amount of pressure on the lens 500, either by pulling on the lens 500 or tapping the upper edge 530 thereof through the crown 60 material, the friction fit is released causing a downward sliding movement of the lens through the slot 75 of the pocket 200. The projecting tabs 540, 550 are free to slide through the lateral slots 242, 252 caused by the displacement between the lateral edges 202, 204 of flap 100 and inner crown 60 material. The downward sliding movement of the lens 500 is halted by contact of the tabs 540, 550 with the fixed lateral ends 72, 74 of the band 70' forming the slot 75. Alternatively, the tabs 540, 550 will contact the lower corners 116, 118 as fixed to the crown 60 if the intermediate band 70' portion is not used. At this extended position the lens 500 is positioned in front of the eyes of the user and generally normal to the overlying bill 50.

Subsequently the user may slide the lens 500 up into the pocket 200 through slot 75 such that the tabs 540, 550 are positioned adjacent the upper corners 110, 112. At such position the above-described friction fit occurs to hold the lens within pocket 200.

Accordingly, the above-described structure provides a lens 500 which is user movable between a first nonfunctional or storage position within the pocket 200 and a second functional position without the pocket 200 and adjacent the eyes of the user. The lens 500 can be either a glare reduction-type of lens or a vision improvement lens according to the desires of the user. The releasable engagement of the lower corners 116, 118 allow different types of lenses 500 to be utilized.

It is to be understood that while a certain form of this invention has been illustrated and described, it is not limited thereto except insofar as such limitations are included in the following claims and allowable functional equivalents thereof.

Having thus described the invention, what is claimed as new and desired to be secured by Letters Patent is as follows:

1. In combination with a headpiece having a crown, an eyeglass system comprising:
    a lens for a user viewing therethrough;
    a flap having a pair of laterally-spaced apart edges and an upper edge and lower edge extending between said laterally-spaced apart edges:
    means for securing at least a portion of each of said flap edges to the crown to form a pocket presenting a pair of laterally-spaced apart slots between said lateral flap edges and the crown and an opening between said lower flap edge and the crown;
    first and second tabs respectively extending in opposed directions from said lens and through said laterally spaced-apart slots upon said lens being positioned within said pocket, said lens slidable between a first position within said pocket and a second position through said opening and in front of the eyes of a user with said tabs being concurrently slidable through said slots.

2. The system as claimed in claim 1 wherein said flap overlies said lens in said first position, said flap cooperating with the adjacent crown to maintain said intermediate lens in said first position.

3. The system as claimed in claim 1 wherein said securing means comprises stitching securing a portion of each of said flap edges to the crown.

4. The system as claimed in claim 1 wherein said tabs engage a portion of said pocket edges secured to the crown at said second lens position, said engagement maintaining said lens at said second position.

5. The system as claimed in claim 1 wherein said securing means comprises:
    at least a first fastener means on said flap;
    at least a second fastener means on the crown engageable with said first fastener means whereby said flap is attached to the crown to form said pocket.

6. The device as claimed in claim 1 wherein said securing means comprises:
    first fastener means at a juncture of each of said laterally-spaced apart edges and said upper and lower edges;
    second fastener means on the crown engageable with said first fastener means, said tabs engaging said engaged fastener means upon movement of said lens to said second position.

7. An eyeglass system comprising:
    a headpiece having a crown for user wearing;
    a lens for user viewing therethrough;
    a generally rectangular flap member having a pair of first and second laterally spaced-apart edges and a pair of spaced-apart edges longitudinally extending between said laterally spaced-apart edges;
    means for connecting a portion of each of said edges of said flap to said crown with the unconnected portions of said flap edges displaced from the crown to form a pair of slots between said crown and said laterally spaced-apart flap edges with an opening spanning said laterally spaced-apart edges between one of said longitudinally extending edges and the crown;
    a pair of tabs extending from said lens and through said slots upon placement of said lens between said flap and said crown, said tabs engaging portions of said edges of said flap connected to said crown upon movement of said lens from a first position adjacent the crown to a second position below the crown, said engagement precluding further movement of said lens beyond said second position.

8. The system as claimed in claim 7 wherein said flap cooperates with the adjacent crown to maintain said lens in said first position intermediate said flap and the adjacent crown.

9. In combination with a headpiece having a crown, an eyeglass system comprising:
    a lens for a user viewing therethrough;
    a pocket attached to a surface of the crown for containing said lens at a first position therein;
    an access opening in said pocket adjacent a lower edge of the crown, said lens slidable through said opening between said first position in said pocket and a second position out of said pocket and below the crown;
    at least one tab extending from said lens;
    at least one slot formed by a displacement of a portion of said pocket from the crown, said slot receiving said at least one tab in extension therethrough and beyond said pocket, said tab engaging a portion of said pocket attached to the crown at said second position, said engagement precluding movement of said tab and lens beyond said second position.

10. In combination with a headpiece having a crown and a bill forwardly extending from a lower edge of the crown, an eyeglass system comprising:
    a lens for a user viewing therethrough;
    at least one tab extending from said lens;
    a material structure connected to the crown for forming at least one slot between said structure and the crown, said slot extending in a direction along the crown and generally normal to the bill, said slot having a first end formed by a first juncture of said structure and the crown adjacent the bill and a second end formed by a second juncture of said structure and crown at a position displaced from the bill, said slot receiving said at least one tab in slidable movement between said first and second ends of said at least one slot to position said lens in a first position adjacent the crown and a second position below the bill.

11. The system as comprised in claim 10 wherein said at least one tab contacts said first juncture upon said lens being in said second position, said contact precluding movement of said lens beyond said second position.

12. The system as claimed in claim 10 wherein said tab contacts said second juncture upon said lens being adjacent the crown, said contact precluding further movement of said lens beyond said first position and towards a top of the crown.

* * * * *